US010378004B2

(12) United States Patent
Mitterer et al.

(10) Patent No.: US 10,378,004 B2
(45) Date of Patent: Aug. 13, 2019

(54) PROTEIN PURIFICATION BY ANION EXCHANGE CHROMATOGRAPHY

(71) Applicants: Baxalta Incorporated, Bannockburn, IL (US); Baxalta GmbH, Zug (CH)

(72) Inventors: Artur Mitterer, Orth/Donau (AT); Meinhard Hasslacher, Vienna (AT); Christian Fiedler, Vienna (AT)

(73) Assignees: Baxalta GmbH, Zug (CH); Baxalta Incorporated, Bannockburn, IL (US)

( * ) Notice: Subject to any disclaimer, the term of this patent is extended or adjusted under 35 U.S.C. 154(b) by 220 days.

(21) Appl. No.: 14/351,541

(22) PCT Filed: Oct. 12, 2012

(86) PCT No.: PCT/EP2012/070257
§ 371 (c)(1),
(2) Date: Oct. 17, 2014

(87) PCT Pub. No.: WO2013/053887
PCT Pub. Date: Apr. 18, 2013

(65) Prior Publication Data
US 2014/0302591 A1    Oct. 9, 2014

Related U.S. Application Data

(60) Provisional application No. 61/547,579, filed on Oct. 14, 2011.

(51) Int. Cl.
*C12N 9/64* (2006.01)
*C07K 1/18* (2006.01)

(52) U.S. Cl.
CPC ............... *C12N 9/644* (2013.01); *C07K 1/18* (2013.01); *C12Y 304/21022* (2013.01)

(58) Field of Classification Search
None
See application file for complete search history.

(56) References Cited

U.S. PATENT DOCUMENTS

| | | | |
|---|---|---|---|
| 4,981,952 A | 1/1991 | Yan | |
| 5,457,181 A | 10/1995 | Michalski | |
| 5,633,350 A * | 5/1997 | Fischer | ............... C07K 14/745 530/380 |
| 5,714,583 A | 2/1998 | Foster et al. | |
| 6,344,596 B1 | 2/2002 | Velander et al. | |
| 6,869,934 B2 | 3/2005 | Mizokami | |
| 7,375,084 B2 | 5/2008 | Scheiflinger et al. | |
| 7,575,897 B2 | 8/2009 | Scheiflinger et al. | |
| 2004/0106779 A1 | 6/2004 | Bigler et al. | |
| 2008/0207879 A1 * | 8/2008 | Artur | ............... C07K 1/18 530/384 |
| 2009/0311239 A1 | 12/2009 | Chtourou et al. | |
| 2010/0047428 A1 | 2/2010 | Lejars et al. | |

FOREIGN PATENT DOCUMENTS

| | | |
|---|---|---|
| EP | 0 363 126 A2 | 4/1990 |
| WO | WO 94/05692 A1 | 3/1994 |
| WO | WO 96/40883 A1 | 12/1996 |
| WO | WO 98/35689 A1 | 8/1998 |
| WO | WO 2006/035058 A2 | 4/2006 |
| WO | WO 2006/067230 A1 | 6/2006 |
| WO | WO 2007/026020 A1 | 3/2007 |
| WO | WO 2007/101681 A1 | 9/2007 |
| WO | WO 2011/073235 A1 | 6/2011 |
| WO | WO 2011/135071 A1 | 11/2011 |
| WO | WO 2013/053887 A1 | 4/2013 |
| WO | WO 2013/053888 A1 | 4/2013 |

OTHER PUBLICATIONS

International Search Report dated Nov. 13, 2012, for International Patent Application No. PCT/EP2012/070257, 4 pages.
Josic, D. et al., "Preparation of vitamin K-dependent proteins, such as clotting factors II, VII, IX and X and clotting inhibitor Protein C," *Journal of Chromatography B*, 2003, vol. 790, pp. 183-197.
Kelley, B.D. et al., "Robustness Testing of a Chromatographic Purification Step Used in Recombinant Factor IX Manufacture," *ACS Symposium Series*, 1998, vol. 698, Chapter 8, pp. 93-113.
Burger, A. et al., "A rapid and efficient purification method for recombinant annexin V for biophysical studies," FEBS, Aug. 1993, vol. 329, No. 1,2, pp. 25-28.
Harrison, S. et al., "The Manufacturing Process for Recombinant Factor IX," *Seminars in Hematology*, Apr. 1998, vol. 35, No. 2, Suppl 2, pp. 4-10.
Osborn, E.C., "The Employment of Deae-Cellulose Columns on a 'Rejection' Principle in the Preparation of Factor VII," *Clinica Chimica Acta*, 1965, vol. 12 pp. 415-418.

* cited by examiner

*Primary Examiner* — Marsha Tsay
(74) *Attorney, Agent, or Firm* — Morgan, Lewis & Bockius LLP

(57) ABSTRACT

The present invention relates to a two-step method for the purification of divalent cation binding proteins with high yield and high purity on anion exchange resin materials, to divalent cation binding proteins obtainable by said method, and to a kit comprising means for carrying out said method.

17 Claims, No Drawings

PROTEIN PURIFICATION BY ANION EXCHANGE CHROMATOGRAPHY

CROSS-REFERENCES TO RELATED APPLICATIONS

The present application is a U.S. National Phase Application of International Patent Application No. PCT/EP2012/070257, filed Oct. 12, 2012, which claims the benefit of U.S. Provisional Patent Application 61/547,579 filed Oct. 14, 2011, which are expressly incorporated herein by reference in their entireties for all purposes.

FIELD OF THE INVENTION

The present invention relates to a two-step method for the purification of divalent cation binding proteins with high yield and high purity on anion exchange resin materials, to divalent cation binding proteins, in particular FIX, preferably obtainable by said method, and to a kit comprising means for carrying out said method.

BACKGROUND OF THE INVENTION

Since the advent of recombinant technology, many mammalian proteins are produced in host cells by e.g. transfecting cells with DNA encoding said proteins and growing the recombinant cells under conditions favorable for the expression of said proteins. The proteins secreted by the cells into the cell culture medium, or residing inside the cells, can be separated from the culture medium and other components using chromatographic techniques, e.g. ion exchange chromatography, affinity chromatography, and the like. For further pharmaceutical applications, purity is of particular importance. However, at the same time the biological activity of the protein must be preserved after thorough purification of the proteins of interest.

The concept of eluting calcium binding proteins from anion exchange resins by divalent cations was firstly reported almost thirty years ago. Although bovine Factor VII was successfully isolated from bovine plasma, the purification of human Factor VII was still problematic, i.e. the material produced was only partially pure or was obtained in such small quantities that it was characterized as activity without detectable protein. Workers in the field succeeded in the isolation of human Factor VII from human plasma in sufficient quantities (with a yield of approx. 30%) by means of adsorbing proteins to a divalent cation, i.e. barium citrate, and then separating the protein by anion exchange chromatography. Further, methods were available for recovering and purifying vitamin K-dependent proteins from the medium of a cell culture producing vitamin K-dependent proteins with different specific activities by means of conventional ion-exchange resins, e.g. anion exchange resins, and using an eluant containing divalent cations, e.g. calcium ion ($Ca^{2+}$), magnesium ion ($Mg^{2+}$), barium ion ($Ba^{2+}$), and strontium ion ($Sr^{2+}$).

Furthermore, methods were available for the purification of Factor IX (FIX) in solution, comprising the steps of applying the solution containing FIX to an anion exchange resin, washing the anion exchange resin with a solution having a conductivity that is less than required to elute FIX from the resin, and eluting FIX from the anion exchange resin with a first eluant including divalent cations to form a first eluate. The first eluate is then applied to a heparin or heparin-like resin to form a second eluate, and the second eluate is applied to hydroxyapatite to form a third eluate, utilizing a high conductivity washing agent in the washing step.

Factor IX (FIX) is a vitamin K-dependent serine protease of the coagulation system, belonging to the peptidase family S1. FIX is inactive unless activated by Factor XIa or Factor VIIa. For its activation, calcium, and membrane phospholipids, are required. Deficiency of FIX causes the hereditary recessive bleeding disorder hemophilia B, which can be successfully treated by administration of posttranslational modified, i.e. phosphorylated and sulfated FIX. FIX can be further converted into activated FIX, i.e. FIXa. As FIXa can negatively affect a given composition of FIX (e.g. by increasing its thrombogenicity as described in the literature), FIX products should preferentially contain a low FIXa content.

Further, Factor VII (FVII) is a vitamin K-dependent serine protease which plays a significant role in the coagulation cascade, where it initiates the process of coagulation with tissue factor (TF). Upon vessel injury, TF is exposed to the blood and circulating FVII. Once bound to TF, FVII is activated to FVIIa by thrombin, Factor Xa, IXa, XIIa, and the FVIIa-TF complex whose substrates are FX and FIX. Furthermore, Annexin V is a cellular protein in the annexin group, having the ability to bind in a calcium-dependent manner to phosphatidylserine and to form a membrane-bound two dimensional crystal lattice. It may play a role in blood coagulation, apoptosis, phagocytosis and formation of plasma membrane-derived microparticles.

Thus, the problem underlying the present invention is to provide an improved method for the purification of divalent cation binding proteins with high yield and high purity. The solution to the above technical problem is achieved by the embodiments characterized in the claims.

SUMMARY OF THE INVENTION

The present invention relates to in a preferred embodiment (item 1)) to a method for the purification of a divalent cation binding protein comprising the steps of:
(a) loading a first anion exchange resin material with the divalent cation binding protein in a loading buffer in the absence or low concentration of divalent cations, optionally followed by one to three wash steps;
(b) eluting the divalent cation binding protein with an eluant comprising a divalent cation and a counter-anion to form an eluate containing the divalent cation binding protein;
(c) diluting the obtained eluate pool, ((1) to optionally lower the conductivity), and increasing the concentration of the divalent cation;
(d) loading a second anion exchange resin material with the eluate as obtained after step (c); and
(e) collecting the flow-through containing the divalent cation binding protein.

In that regard, step (a) as described above is preferably carried out the absence of free divalent cations. "Free" divalent cations in that context shall mean non-complexed divalent cations. That is, if e.g. approximately 1 mM $Ca^{++}$ was present complexed to EDTA, that would still be considered to be in the absence of (free) divalent cations.

The optional step C(1) of lowering the conductivity is necessary only, if the conductivity has not already been lowered in the last optional wash step; preferably, the lowering of the conductivity is carried out in wash step 3, as described in more detail below.

2. The method according to item 1, wherein after the loading step one or more washing steps (1), (2) and/or (3) with a washing buffer (1), (2) and/or (3) in the absence of a divalent cation but in the presence of a counter anion is/are performed.

Preferred counter-anions are: chloride (most preferred), acetate, phosphate, sulfate, carbonate, though not limited to these.

3. The method according to item 1 or 2, wherein at least one of the loading buffer and/or washing buffer, has/have a pH that is at least 0.5 pH units lower than the pH of the eluant of step (b), preferably wherein either the loading buffer and/or the buffer in wash step (2) has/have a pH that is at least 0.5 pH units lower than the pH of the eluant of step (b).

4. The method according to any one or more of items 1 to 3, wherein the eluant in step (b) has a conductivity that is higher than the conductivity of the loading buffer in step (a) and the optional washing buffer and wherein the supplemented eluate in step (c) has a conductivity that is lower than the conductivity of the eluant in step (b).

In a preferred embodiment, the conductivity of the elution buffer is between 16 and 25 mS/cm (RT), preferably 19-20 mS/cm (RT). If the optional wash step 2 is performed ("acidic wash") the conductivity is preferably between 14 and 19 mS/cm (RT), more preferred between 16 and 18 mS/cm (RT) whereby in all cases the requirement of item 4 above should be fulfilled.

5. The method according to any of items 1 to 4, wherein the at least one divalent cation in step (b) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof.

6. The method according to any one of items 1 to 5, wherein the first and second anion exchange resin materials each have a positively charged group which is independently selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

7. The method according to any one of items 1 to 6, wherein the first and second anion exchange resin materials each carry a primary amine as ligand which is independently selected from the group, consisting of aminohexyl, benzamidine, lysine, and arginine.

8. The method according to any one of items 1 to 7, wherein the divalent cation binding protein is a calcium binding protein.

9. The method according to any one of items 1 to 8, wherein the divalent cation binding protein is a vitamin K-dependent protein.

10. The method according to any one of items 1 to 9, wherein the divalent cation binding protein is selected from the group, consisting of Factor II, Factor VII, Factor IX, Factor X, Protein C, Protein S, Annexin and calmodulin, particularly preferred from the group consisting of Factor IX (FIX), Factor VII (FVIIa) and Annexin V.

Any one of the above proteins can be derived either from a natural source, e.g. plasma, or from recombinant technologies.

11. The method according to any one of items 1 to 10, wherein the pH in step (a) is 6.8 to 7.5, preferably 7.0 to 7.4, for a case where an optional wash step is performed and is pH is 5.5 to 6.5, preferably 5.9 to 6.1 in a case where the optional wash step is not performed.

12. The method according to any one of items 1-11, wherein the pH of the optional wash step (3) is between 7.0 to 8.2, preferably between 7.3 to 8.0, even more preferred 7.3-7.5.

13. The method according to any one of items 2 to 12, wherein the pH in the optional wash step (1) is at 7.3-7.5, and the pH of the optional wash step (2) is preferably 5.5 to 6.5, preferably 5.9 to 6.1.

14. The method according to any one of items 1 to 13, wherein the elution buffer (i.e. eluant) in step (b) contains calcium and has a pH of 7.5 to 8.5, preferably 7.8 to 8.2.

15. A method according to any of items 1-14 above, particularly according to item 3, wherein the pH of the loading buffer in loading step (d) is higher than either the pH of the loading buffer in loading step (a) or the pH of the wash, which follows after loading (a).

The "wash which follows after loading (a)" in the context above and as also mentioned below, refers here to the "acidic wash" or wash 2.

16. A method according to any of items 1-15 above, particularly according to item 3, wherein the conductivity in the loading step (d) is equal to or lower than the conductivity of the wash, which follows after loading (a).

17. A method according to any of items 1-16 above, particularly according to item 3 above, wherein the concentration of divalent cations of the loading buffer in step (d) is higher than the concentration of divalent cations in the elution buffer of step (b).

18. The method of any of items 1-17, wherein the step of providing the obtained eluate pool with a low conductivity is carried out by dilution with an appropriate dilution buffer, alternatively by changing the buffer composition, or alternatively by dialysis, diafiltration or gel-filtration.

19. A divalent cation binding protein, as obtained by the method according to any one of items 1-18 above below.

20. (r)FIX, obtained by the method according to any one of items 1-18 above.

21. (r)FIX according to item 20, with a specific activity of at least 270 I.U./mg FIX Ag, preferably a specific activity of 270 to 350 I.U./mg FIX Ag, more preferred a specific activity of 270 to 320 I.U./mg FIX Ag, particularly preferred with a specific activity of 280 to 300 I.U./mg FIX Ag.

22. Pharmaceutical composition comprising (r)FIX as defined in item 20 or 21, with a CHO HCP reduction ratio of about 2.5-3 log reduction.

The 2.5-3 log reduction is the log of the overall reduction of CHO HCP, as also derivable from Table 4 below, which shows the CHO HCP reduction as 229 (from step 1 to step 2) and 1.75 (from step 2 to step 3), i.e. 1.75×229=approx. 440, the log thereof would be 2.6.

23. Pharmaceutical composition comprising (r)FIX as defined in item 20 or 21, and/or according to item 22, with a CHO HCP impurity of less than 50 μg/mg FIX Ag, preferably less than 20 μg/mg FIX Ag, even more preferred less than 10 μg/mg FIX Ag.

24. Pharmaceutical composition comprising (r)FIX as defined in item 20 or 21, and/or according to item 22 or 23, wherein the composition comprises less than 10 μg/ml CHO DNA, preferably less than 5 pg/ml CHO DNA, even more preferred less than 1 pg/ml CHO DNA.

25. Pharmaceutical composition comprising (r)FIX as defined in item 20 or 21, and/or according to any one of items 22-24, wherein the (r)FIX composition comprises less than 1 mU FIXa (activated FIX) activity/unit FIX clotting activity, preferably less than 0.75 mU FIX activity/unit FIX clotting activity, more preferred less than 0.5 mU FIX activity/unit FIX clotting activity, even more preferred less than 0.3 mU FIX activity/unit FIX clotting activity.

1 mU FIXa activity/unit FIX clotting activity is equivalent to 0.1% chromogenic activity per IU/ml FIX clotting activity (see assay method as described below)

26. A kit comprising means for carrying out the method according to any one of items 1-18.
27. (r)FIX composition, obtainable by the method of any one of items 1-18, wherein the (r)FIX composition comprises less than 1 mU FIXa (activated FIX) activity/unit FIX clotting activity, preferably less than 0.75 mU FIX activity/unit FIX clotting activity, more preferred less than 0.5 mU FIX activity/unit FIX clotting activity, even more preferred less than 0.3 mU FIX activity/unit FIX clotting activity.
28. (r)FIX composition according to item 27, further characterized by one or more of the features as defined in any one of items 20-24.
29. (r)FIX composition, wherein the (r)FIX composition comprises less than 1 mU FIXa (activated FIX) activity/unit FIX clotting activity, preferably less than 0.75 mU FIX activity/unit FIX clotting activity, more preferred less than 0.5 mU FIX activity/unit FIX clotting activity, even more preferred less than 0.3 mU FIX activity/unit FIX clotting activity.
30. (r)FIX composition according to item 29, further characterized by one or more of the features as defined in any one of items 20-24.

In a particularly preferred embodiment, the present invention pertains to the following method:

Preferably, elution (b) is carried out with an elution buffer containing 1.8-2.2 mM calcium at a pH of 7.8-8.2.

Preferably step (c) is carried out with a calcium-containing buffer to adjust the calcium concentration to 5-7 mM and to reduce conductivity to 15-18 mS/cm (RT), resulting in a pH of 7.4-7.8.

Thus, the present invention also relates to purified divalent cation binding proteins obtainable by the above method, and to a kit comprising means for carrying out the above method. The present invention accordingly also relates to FIX, preferably recombinant FIX, which is obtainable by the inventive method or has been obtained by the inventive method. The present invention also relates to FIX or FIX compositions, preferably recombinant FIX or FIX compositions with a low content of FIXa. Such a FIX or FIX composition can be obtainable by or has been obtained by the inventive method.

DETAILED DESCRIPTION OF THE INVENTION

In one aspect, the present invention relates to method for the purification of a divalent cation binding protein comprising the steps of:
(a) loading a first anion exchange resin material with the divalent cation binding protein in a loading buffer in the absence or low concentration of divalent cations, optionally followed by one two three wash steps;
(b) eluting the divalent cation binding protein with an eluant comprising a divalent cation and a counter-anion to form an eluate containing the divalent cation binding protein;
(c) diluting the obtained eluate pool, ((1) to optionally lower the conductivity), and increasing the concentration of the divalent cation;
(d) loading a second anion exchange resin material with the eluate as obtained after step (c); and
(e) collecting the flow-through containing the divalent cation binding protein.

The present inventive method uses a procedure on two anion exchange columns with the first column being operated in a product binding mode and the second column being operated in a product non-binding mode. The principle of the procedure requires in a preferred embodiment contacting (i.e. loading) the cation binding protein (e.g. rFIX) solution with (on) a first anion exchange resin at a neutral or acidic pH (pH=6.8-7.5, pref. 7.0-7.4, e.g. 7.0-7.2) in the presence of a chelator, e.g. EDTA. EDTA can be preferred if the product yield shall be further improved. EDTA can improve the binding of the divalent cation binding protein, e.g. FIX. In a preferred embodiment, after a wash (at e.g. a pH as defined more in detail below) followed by a wash at low conductivity the product (wherein this wash would be the wash immediately preceding the elution) is eluted with a buffer containing e.g. calcium (with a pH of e.g. about 8.0). The obtained eluate pool is diluted to lower the conductivity and increase the calcium concentration. The diluted solution has a pH of e.g. 7.6-7.8. The conditioned eluate pool of the first anion exchange purification step is then transferred (e.g. pumped) onto the second anion exchange column where the cation binding protein, like e.g. rFIX, does not bind under the conditions applied (in particular presence of increased concentrations of divalent cations, and slightly basic pH and a conductivity of about 15-21 mS/cm (RT)), whereas protein impurities do bind. The resulting cation binding protein, e.g. rFIX, contained in the column effluent of the second anion exchange purification has a high purity and high specific activity.

The term "in the absence of divalent cations" as used herein refers to the absence of free divalent cations in the buffer, wherein divalent cations that are bound to a protein or complexed e.g. by a chelator, e.g. EDTA, may be present. The term "at a low concentration of divalent cations" refers to a divalent cation concentration in the µM range, in particular a concentration of 1000 µM at most, preferably 800 µM at most, even more preferred 500 µM at most. For this application the term "in the absence of divalent cations" is meant to also encompass the above definition for "at a low concentration of divalent cations".

As already mentioned above, protein bound calcium, e.g. EDTA bound calcium can be tolerated in one embodiment. If the calcium is bound to a protein, it is considered "inactive" calcium in the context of this invention. It does then not interfere with product binding. Free calcium, on the other hand, could interfere with product binding.

Loading (a) of the first anion exchange resin material with the divalent cation binding protein in a loading buffer in the absence of divalent cations can be carried out by any method known in the art. In particular, conditions suitable for loading the divalent cation binding protein to the anion exchange resin material are well known to a person skilled in the art. The specific conditions for the conductivity of the loading buffer that allows binding of the product depend on the particular properties of the protein and the anion exchange resin material used (e.g. ligand density, ligand presentation, etc.). Divalent cations bind to proteins in regions that are usually highly acidic (i.e. negatively charged). The negative charges are masked when the divalent cation is bound. However, by loading the anion exchange material with the divalent cation binding protein in the absence of divalent cations, e.g. by stripping off the bound divalent cation by a chelator, e.g. EDTA, the protein carries highly negatively charged patches on the surface that allow strong binding to an anion exchange ligand. The conditions for loading a protein onto an anion exchange resin material further always require a balance between pH and the concentration of the counter-ions, e.g. Cl⁻. The chemistry of the counter-ion also influences the elution behavior, e.g. Cl⁻ carries one negative charge, and phosphate at neutral pH carries two negative charges. The latter can have a higher eluting power compared to Cl⁻, even when the conductivity is lower.

The loading of Anion Exchange column 1 (i.e. step (a)) is preferably performed at a pH of 6.8-7.5, preferably 7.0-7.4, followed by a wash 1 at a pH of 7.3-7.5 to complete loading, a wash 2 at acidic conditions (pH 5.5-6.5, preferably 5.8-6.2, more preferably 5.9-6.1). In a further embodiment an optionally wash 3 (low conductivity wash, this is the wash which is carried out directly before elution) at pH 7.0-8.2, preferably 7.3-8.0, e.g. pH 7.3-7.5 to prepare the column for elution can be carried out. The elution is performed at a pH of 7.5-8.5, more preferably 7.8-8.2. It is one of the features of the present invention that the pH of the elution buffer is at least 0.5 pH units higher than the pH of the preceding wash 2 (high conductivity wash, see conductivity conditions as described above). This second, "acidic" high conductivity wash still has a conductivity which is lower than the conductivity of the elution.

In the most preferred embodiment, the loading step of the first anion exchange is carried out at a neutral to slightly acidic pH, e.g. at a pH of 6.8-7.5, preferably 7.0 to 7.4, if the optional washing step(s) is (are) performed. Preferably this loading step is followed by a first wash at pH=7.3-7.5 to complete loading, a second wash at acidic conditions (pH 5.5 to 6.5, preferably 5.8 to 6.2) and a wash 3 at a pH of 7.3-7.5 to prepare the column for elution. The pH of the loading step of the first anion exchange column is set at 5.5 to 6.5, more preferred at pH 5.9-6.1, if the optional washing step(s) is (are) not performed. In particular, it is one of the features of the present invention that the pH needs to be increased, preferably by at least 0.5 pH units before the elution step is carried out. This increase can occur at all stages, e.g. from the loading step directly to the elution step, if no wash steps are carried out in between. In an alternative embodiment, the pH increase occurs after an acidic wash, as described above. The elution is—as described below—preferably carried out at a pH of 7.5-8.5, more preferably 7.8-8.2.

In a case where only one wash step is carried out, i.e. wash step (1), this wash step will be carried out without addition of salt; consequently, the pH is of not immediate importance in the wash step, as long as the pH is finally increased in the elution step by at least 0.5 pH units compared to the loading step.

In one preferred embodiment, where two wash steps are carried out, i.e. wash steps (1) and (2), or where only the stringent wash step (2) (see also below) is carried out, this loading buffer could have a pH in the neutral to slightly acidic area, as defined above, though that would be allowable according to the inventive principles only if the second wash step (i.e. wash step 2) had a lower pH of 5.5 to 6.5, or 5.9-6.1. If the loading step was already carried out at this lower pH, than the wash step (2) would preferably also have this lower pH. Wash step (2) in a preferred embodiment is carried through at a high conductivity, as defined above.

In a further preferred embodiment, where three wash steps are carried out, i.e. wash steps (1), (2) and (3), the wash step (3) would preferably not contain any salt; consequently, the pH in this step would not be relevant, as long as the above conditions as mentioned for the case with two wash steps are provided for and the pH is increased in the elution step by at least 0.5 pH units, compared preferably to the loading and/or the wash step (2). Wash (3) is preferably a low conductivity wash (in that case, step c(1) need not be carried out, if the conductivity of the resultant eluate is already low).

In a particularly preferred embodiment, the pH in the wash step (3) can already be increased to the level of the pH of the elution step. Thus, the preferred pH of wash step (3) is between 7.0 and 8.2, preferably between 7.3 and 8.0, even more preferred at 7.3-7.5. If the wash step (3) is performed at this particular pH condition the present inventors found that the degree of impurities which are comprised in the eluted desired product is further reduced compared to a situation where no wash step (3) is performed or where said step is performed at a different pH, e.g. at a pH which is still as low as the pH used during loading and/wash steps (1) and (2). The inventors believe, though they do not wish to be bound to that hypothesis, that adjusting the pH of the wash step (3) to the same pH as the elution avoids a pH gradient during elution. A pH gradient during elution could be a source of interference which allows some impurities to be co-eluted with the product. Wash 3 as described above conditions the column advantageously for elution. A high pH and low conductivity of this wash prevent co-elution of impurities during the following elution.

Even more preferred, the wash step (3) should have a conductivity, and in particular an elution power which is very low or even close to zero. Such a very low conductivity would be preferably at 1-15 mS/cm (RT), more preferably below 5 mS/cm (RT).

In a preferred embodiment, the loading step (a) comprises a solution comprising proteins, the desired product, and all compounds of the cell culture media including amino acids, vitamins, sugars, trace metals etc (including KCl, NaCl, Ca, ca. 13 mS/cm (RT)). After the loading step, a washing step 1 is preferably carried out which is then completing the loading (preferably close to or at neutral pH and at a low conductivity). Thereafter, preferably a second washing step 2 follows, which is considered a stringent wash, and is preferably carried out with a low pH and 150 to 210, preferably 170 to 190 mM, most preferred 180 mM (if carried out with NaCl, preferred conditions for different salts would be within the knowledge of the person skilled in the art), followed in a further preferred embodiment by a washing step 3 which is preparing the loaded column for the elution. This third wash step is preferably carried out at a low conductivity and at a pH as defined above. This washing step has the major task to reduce the conductivity in the column and bring the pH back to neutral as the previous wash was at low pH, and even bring the column close to the pH of the elution, as explained above. These measures prepare the column for the pseudo-affinity elution with Calcium and prevent co-elution of impurities in the interface between elution buffer and wash-2 buffer.

The elution is preferably carried out with a buffer containing a divalent cation and 150 to 210, preferably 170 to 190 mM and most preferred 180 mM NaCl. Other counter anions would be possible, in addition to the above chloride (most preferred), e.g. acetate, phosphate, sulfate, carbonate, though not limited to these, and at a pH of 7.5 to 8.5, preferably 7.8 to 8.2 and most preferred a pH of 8.0, in any case a pH which is at least 0.5 pH units higher than the pH used during loading and optionally during washing preferably during wash 2.

Further, suitable loading buffers for loading a divalent cation binding protein to an anion exchange material in step (a) of the method of the present invention, providing conditions under which the divalent cation binding protein is bound to the anion exchange material are well known in the art. For example, the loading buffer can have a pH of pH 6.8 to 7.5, preferably of pH 7.0 to 7.4, if an optional washing step (s) is (are) carried out, as explained above. It may contain any salt concentrations suitable for binding the divalent cation binding protein to the anion exchange resin material which may be easily determined by a person skilled in the art. In a preferred embodiment, the loading buffer may contain a chelating agent, e.g. EDTA, preferably 0.5 to 10 mM EDTA, more preferred 1 to 5 mM EDTA, preferably approximately 2 mM EDTA. Alternative possible chelating agents can also be used and are well known to a person skilled in the art. A loading buffer containing the divalent cation binding protein which may be applied to the anion exchange resin material in the method of the present invention may contain for example 20 mM MES and 2 mM EDTA. MES is an example for a buffering agent for pH 6; for pH 7 and above it would e.g. be possible to use Tris buffer. As the loading material is in a preferred embodiment a cell culture supernatant, which is basically buffered by carbonate and amino acids, a loading buffer must not necessarily be present.

The method of the present invention preferably comprises the step of washing the loaded anion exchange resin material with a washing buffer in the absence of divalent cations. This washing step can be carried out by any method known in the art. Suitable washing buffers for washing impurities off the anion exchange material essentially without eluting the divalent cation binding protein are well known in the art. For example, the washing buffer has a pH which is at least 1.0 or at least 0.5 pH units lower than the pH of the loading buffer and is preferably 5.5-6.5, preferably 5.9-6.1. It may contain any salt concentrations suitable for washing the anion exchange resin material without eluting the divalent cation binding protein in a significant amount which may be easily determined by a person skilled in the art. For example, the washing buffer may contain a suitable buffer agent like for example Bis-Tris, acetate buffer, citrate buffer or phosphate buffer, preferably 20 mM Bis-Tris. Preferably, the washes 1 and 3 have Tris as washing buffers while wash 2 has MES. Additionally, it may contain a chelating agent like for example EDTA, preferably 0.5 to 10 mM EDTA, more preferred 1 to 5 mM EDTA, preferably approximately 2 mM EDTA. Further, it may contain a suitable salt, e.g. salts of the following cations and anions: $K^+$, $Na^+$, $Li^+$, $NH_4^+$ and anions like chloride, phosphate, sulfate, carbonate, acetate, for regulating the conductivity of the washing buffer, like for example NaCl, which may be present in a concentration of ≤200 mM, preferably from 100 mM to 200 mM, more preferably from 150 mM to 200 mM, more preferably from 170 mM to 190 mM, and most preferably from 175 mM to 185 mM. In another preferred embodiment of the present application, the washing buffer contains 100 to 200 mM NaCl. The absolute value for the salt concentration depends on the divalent cation binding protein to be purified, wherein it is within the knowledge of the person skilled in the art to determine which divalent cation binding proteins require lower or higher salt concentrations to get the optimal purity.

Preferably, according to the present method for purification of divalent cation binding proteins, a second wash step is carried out after the above-mentioned first wash step. This wash step, if being the wash directly before elution, is carried out at a low conductivity. This conductivity is preferably lower than the conductivity in the loading and the first wash step. Even more preferably, a third wash step can be performed. This embodiment has been described above in detail.

Eluting the divalent cation binding protein with an eluant comprising a divalent cation can be carried out by any method known in the art. In particular, suitable eluants containing suitable counter-cations are well known in the art. Preferred counter-cations include $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, or combinations thereof. Most preferred is calcium. The elution buffer preferably has a pH which is higher than the pH of the wash buffer. The pH is preferably increased by at least 0.5, preferably 1.0 pH units. Very preferably the elution buffer has a pH of between 7.5 and 8.5, even more preferred 7.9 to 8.1. It may contain any salt concentrations suitable for eluting the divalent cation binding protein from the first anion exchange resin material without eluting impurities in a significant amount which may be easily determined by a person skilled in the art. For example, it may contain a suitable buffer agent like for example HEPES, Tris, preferably 20 mM Tris, Tris/acetate, histidine, Gly-Gly, MOPS, or tricine, at concentrations ranging typically from 5 to 50 mM. It may also contain a suitable salt, e.g. salts of the following cations and anions: $K^+$, $Na^+$, $Li^+$, $NH_4^+$ and anions like chloride, phosphate, sulfate, carbonate, acetate, for regulating the conductivity of the buffer, like for example NaCl, which may be present in a concentration of 150-200 mM.

The following is a list of particularly preferred buffers:
Tris: buffers at pH=8.06±1.0,
HEPES: buffers at pH=7.7±1.0,
MOPS; buffers at pH=7.3±1.0,
Tricine: buffers at pH=8.3±1.0,
Histidine: buffers at pH=7.6±1.0,
Gly-Gly: buffers at pH=7.4±1.0,
Bis-Tris: buffers at pH=6.35±1.0,
ACES (N-(2-Acetamido)-2-aminooethanesulfonic acid): buffers at pH=7.0±1.0,
ADA (N-(2-Acetamido)-iminodiacetic acid): buffers at pH=7.0±1.0,
MES: buffers at pH=approx. 6.0.

The elution buffer may also contain a suitable salt for regulating the conductivity of the washing buffer, like for example NaCl, which may be present in a concentration of 100-200 mM. The absolute value for the salt concentration depends on the divalent cation binding protein to be purified, wherein it is within the knowledge of the person skilled in the art to determine which divalent cation binding proteins require lower or higher salt concentrations to get the optimal purity.

After the elution step, the eluate pool obtained is diluted to lower the conductivity and the concentration of divalent cations, preferably the calcium concentration is increased. This measure provides conditions that prevent binding of the product to the second Anion Exchange resin and facilitates binding of host cell proteins. Such a dilution is known to a person skilled in the art and is conducted according to well known methods. For example, the addition of one column volume dilution buffer increases Ca and slightly reduces the conductivity. The diluted solution preferably has final pH of 7 to 8, more preferably 7.5 to 7.9.

The person skilled in the art understands that further procedures to provide the obtained elutate pool with the decreased conductivity would also fall under the definition of diluting the eluate pool to lower the conductivity. Thus, further possibilities to lower the conductivity of the eluate pool would be changing the buffer composition, e.g. by dilution with a low salt buffer or by dialysis, or by using diafiltration.

As used herein, the term "anion exchange resin material" does not underlie a specific restriction. According to the present invention, the first and second resin includes any material suitable for anion exchange chromatography known in the art, like for example an agarose based chromatography material, e.g. sepharoses like Fast Flow or Capto, polymeric synthetic material, e.g. polymethacrylate like Toyopearls, polystyrene/divinylbenzene, e.g. Poros, Source, or cellulose, e.g. Cellufine. In a specific example of the present invention, the first and second anion exchange resin material is sepharose, which is based on modified agarose, the polysaccharide chains of which are crosslinked to form a three-dimensional network. In a preferred embodiment, the first and second anion exchange resin materials include, but are not limited to resins that carry a primary amine as ligand, e.g. aminohexyl sepharose, benzamidine sepharose, lysine sepharose, or arginine sepharose. In another preferred embodiment, the first and second anion exchange resin materials include, but are not limited to resins having a positively charged moiety at neutral pH, such as alkylaminoethane, like diethylaminoethane (DEAE), dimethylaminoethane (DMAE), or trimethylaminoethyl (TMAE), polyethyleneimine (PEI), quaternary aminoalkyl, quaternary aminoethane (QAE), quaternary ammonium (Q), and the like. In a particularly preferred embodiment, the anion exchange resin material is Q-Sepharose Fast Flow (Q-Sepharose FF). According to the method of the present invention, the first and second anion exchange resin materials may be the same or may be different.

The loading buffer (step d) for the second anion exchange step can be the same as above for the first anion exchange step. The difference between the two anion exchange steps as provided according to the present invention is essentially the following:

a) The first anion exchange column is loaded with the starting material, i.e. in a preferred embodiment with the cell culture material. This is a highly impure starting material. The second anion exchange column is loaded with material which has already been purified to some extent, as it is the material obtained after the elution (and supplementation) step.

b) The first anion exchange step is carried out with divalent cations, for the elution of the product, after having loaded the first anion exchange column in the absence of divalent cations.

c) The pH and the concentration of the divalent cations of the load for the second anion exchange is selected in a preferred embodiment so that the pH of load (d) is higher that the pH of either the (acidic, e.g. wash 2) wash after the load (a) or the load (a) per se if no wash steps are used. Furthermore, the conductivity of load (d) is comparable to the acidic wash, but preferably lower, if this wash is carried out. The divalent cation concentration, i.e. $Ca^{++}$ concentration is higher in the load (d) than in the elution buffer of step (b).

d) Consequently, on the first anion exchange column the product binds to the column and on the second anion exchange column the product does not bind.

The divalent cation binding protein according to the present invention may be any divalent cation binding protein, like for example a calcium binding protein and/or a vitamin K-dependent protein. In a preferred embodiment, the divalent cation binding protein is selected from the group, consisting of Factor II, Factor VII, Factor IX, Factor X, Protein C, Protein S, Annexin and calmodulin, particularly preferred from the group consisting of Factor IX, Factor VII and Annexin V.

The starting material ("sample") for the divalent cation binding protein may be obtained using methods known to a person skilled in the art like, e.g. plasma derived proteins, transgenically produced proteins, or recombinantly produced proteins, for example using CHO cells. Secretory and non-secretory methods for extracting proteins from cell culture are well known to a person skilled in the art. This may include any method known in the art for (i) the production of recombinant DNA by genetic engineering, e.g. via reverse transcription of RNA and/or amplification of DNA, (ii) the introduction of recombinant DNA into pro-karyotic or eukaryotic cells by transfection, e.g. via electroporation or microinjection, (iii) the cultivation of said transformed cells, e.g. in a continuous or batchwise manner, (iv) the expression of a divalent cation binding protein, e.g. constitutive or upon induction, and (v) the isolation of the protein, e.g. from the culture medium or by harvesting the transformed cells, in order to obtain a crude divalent cation binding protein. Additionally, the recombinant DNA encoding a divalent cation binding protein, e.g. a plasmid, may also contain a DNA sequence encoding a selectable marker for selecting the cells which have been successfully transfected with the recombinant DNA.

In a preferred embodiment of the present invention, the starting material for the inventive method is a material comprising FIX, preferably plasma comprising FIX or recombinantly produced FIX. The recombinant production of FIX is well known in the art. rFIX, which is recombinant FIX, is according to a preferred embodiment secreted in the cell culture supernatant (CCS) and this CCS is then used as a starting material for the present inventive method.

The proteins may be pre-purified to reduce impurities, for example by gel electrophoresis, chromatography, gel filtration, centrifugation, filtration, precipitation, crystallization or any other method known in the art. The term "impurity" as used herein includes any impurity originating from the production of the divalent cation binding protein and may include e.g. host cell protein (HCP) impurities, nucleic acid impurities, polypeptide impurities, buffer and salt impurities, impurities originating from the cell culture medium, product related impurities, such as dimers or fragments, and combinations thereof.

The inventive method as described herein allows the removal or separation of inactive and truncated forms of e.g. FIX from the active FIX product. The method also allows to control or keep the formation of product related impurities at a very low level (e.g. degradation products, product aggregation, particles). Even further, the method provides conditions to keep the amount of activated FIX (FIXa) at a particularly low level. In addition, the method is particularly powerful in separating off of process related impurities (CHP HCP, CHO DNA, media components) from the active FIX product.

A further impurity which is encountered in particular in FIX preparations, even FIX pharmaceutical preparations, is activated FIX, i.e. FIXa. It has been shown that FIXa negatively affects the desired resultant FIX preparation as it raises thrombogenicity. Thus, it is highly desirable to provide methods to reduce the content of FIXa in an FIX preparation.

The present inventive method achieves this goal by preventing the formation of FIXa in the preparation which is obtainable by the present method.

In an advantageous and surprising way, it is also possible according to the present invention to reduce the content of host cell protein (HCP), in particular CHO cell HCP if the starting material used is a recombinantly produced FIX in a cell culture or cell culture supernatant.

In a further advantageous and surprising way, it is additionally possible to reduce the content of host cell DNA, in particular CHO DNA in the composition obtainable by the present inventive method.

The above results are further to the improvements in yield and specific activity which are provided by the present invention.

In a preferred embodiment, the divalent cation binding protein which has been purified according to the method of the present invention has a purity with respect to host cell protein (HCP) impurities of at least 95% w/w, more preferably at least 98% w/w, more preferably at least 99% w/w, and most preferably at least 99.5% w/w divalent cation binding protein in total protein. Accordingly, in a preferred embodiment, the content of the HCP impurities in the purified divalent cation binding protein is less than 5% w/w, more preferably less than 2% w/w, more preferably less than 1% w/w, and most preferably less than 0.5% w/w. The percentage values of the HCP impurities refer to w/w of product, i.e. the purified divalent cation binding protein, and can be measured, for example, by HPLC or ELISA.

Further, in another aspect of the present invention, a purified divalent cation binding protein is provided which is obtainable by or has been obtained by the method of the present invention as Also, a kit is provided comprising means for carrying out the method of the present invention. In particular, the kit of the present invention may contain a loading buffer and/or an eluant and/or a washing buffer and/or a solution of divalent cations which are suitable for the purification of a divalent cation binding protein using an anion exchange resin material according to the present invention. In a preferred embodiment, the loading buffer, the washing buffer and/or the eluant are as defined above. Further, the kit of the present invention may contain a suitable anion exchange resin material.

The present invention further relates to the use of the method of the present invention as defined above and/or of the kit of the present invention as defined above for the purification of a divalent cation binding protein.

The present invention provides an efficient method for the purification of a divalent cation binding protein using anion exchange resin materials allowing a high reduction of process related impurities of the protein with concomitantly high product yields.

The eluate pool which has been diluted of the first anion exchange purification step is then loaded onto the second anion exchange column, where the divalent cation binding protein will not bind under the conditions applied. The resulting divalent cation binding protein contained in the column affluent of the second anion exchange purification has a high purity and high specific activity. Furthermore, it has a low content of (CHO) HCP, a low content of (CHO) DNA and a low content of FIXa.

The content of Factor FIXa is measured by way of its activity, expressed as percentage activity relative to Factor IX activity.

The potency (in international units, IU) of a recombinant FIX (rFIX) product, is determined using a widely known and accepted in vitro one-stage clotting assay using a reference calibrated against the World Health Organization (WHO) International Standard for Factor IX concentrate. One international unit is the amount of FIX activity present in 1 mL of pooled, normal human plasma.

FIXa in said product is measured using an assay which is generally well known to a person skilled in the art. One example is the commercially available chromogenic FIXa kit (like Rox FIX-A, article No 950030; Rossix, Molndal, Sweden) employing a reference calibrated against the World Health Organization (WHO) International Standard for Factor IXa. To carry out such an assay, human FX is activated to FXa by FIXa in the presence of FVIII, thrombin, calcium and phospholipids. The amount of FXa generated is measured with a specific FXa substrate, which upon cleavage will liberate p-nitroaniline in amounts that are proportional to those of FXa. The assay is very sensitive to FIXa with a lower limit of quantification of 0.10 mIU/mL.

The levels of pre-activated FIX (rFIXa) in the final product (as obtained by the present inventive method) were consistently very low. The allowed limit is set as ≤0.10% FIXa activity (chromogenic IU/mL)/FIX activity (clotting IU/mL). The actual FIXa content of 15 tested batches of the invention was however as low as ≤0.02% FIXa/FIX. All FIX preparations, which were obtained following the presently claimed purification process, had values of less than 0.02% FIXa/FIX. When a single BeneFIX lot (E94791 as comparative product available on the market) was analyzed with the same assays, the relative FIXa content was measured as 0.11%.

Taken together, the relative FIXa content of all lots was consistently low and apparently up to 10-fold lower than that of the comparative product.

In particular, the method of the present invention is based on the following principles. Generally, binding of proteins to anion exchange resin materials is increased at lower conductivities and higher pH values. Vice versa, binding of proteins to anion exchange resin materials is decreased at higher conductivities and lower pH values. In the method of the present invention, the divalent cation binding protein is preferably loaded and/or washed at a low pH, as explained in detail above, which still allows binding of the divalent cation binding protein to the first anion exchange material and does not harm the structural integrity or the activity of the divalent cation binding protein. Many protein impurities will not bind to the first anion exchange resin material, and, therefore, binding of impurities to the first anion exchange resin material is greatly reduced while the product indeed does bind to the first anion exchange column. Protein impurities that do bind to the first anion exchange resin material under these conditions, and did not get washed off are prevented from co-elution by increasing the pH during elution. The increase of the pH in the eluant causes all proteins to bind even stronger to the first anion exchange resin material, but the divalent cation specifically interacts with the product causing elution. The eluate of the first anion exchange column is conditioned to adjust the conductivity (equal to or lower compared to the acidic wash, as described above), increase the pH (at least 0.5 higher than the load (a) or the acidic wash) and increase the concentration of divalent cations (to be higher than in the load (a)). These measures provide the conditions for selective binding of impurities and selective non-binding of the product on the Anion Exchange resin. According to the method of the present invention, only the divalent cation binding protein does not bind to the second anion exchange material due to the divalent cations present in the eluate. In this context, it should be noted that increasing the pH during elution in step (b) is very atypical for an anion exchange elution procedure and increasing the pH for loading in step (d) compared to the acidic wash is very atypical for a negative chromatography, i.e. an anion exchange chromatography wherein the protein to be purified is expected in the flow-through, since—as has been stated above—proteins generally bind stronger to anion exchange resin materials at higher pH values. By using the eluate from the first anion exchange resin material with at least one divalent cation, the method of the present invention surprisingly and advantageously achieves superior purities of the divalent cation binding protein product by anion exchange chromatography.

In particular, the increase of pH during the Ca-induced product elution of step (b) (elution buffer has higher pH than load buffer of step (a) or acidic wash of step (a)) and the adjustment of the load for step (d) (pH higher than acidic wash of step (a), divalent cations higher than eluant of step (b)) provides for a selective purification of divalent (Ca) binding proteins and prevents co-elution of impurities. The loading of the second anion exchange resin material at high pH and high calcium (as an example for divalent cations) forces impurities to bind to the second anion exchange resin material while binding of the protein to be purified is inhibited by supplementing divalent cations. According to the present invention, the above conditions result in a high purity as well as high yields of divalent cation binding proteins. The method of the present invention may provide a significant reduction of process related polypeptide impurities e.g. by loading the protein solution onto an anion exchange resin material at reduced pH, eluting the product with an eluant with at least one divalent cation at increased pH, and loading the eluate onto a second anion exchange resin material under high pH, and increased concentration of divalent cations, and collecting the flow-through.

Various modifications and variations of the described method and products of the invention will be apparent to those skilled in the art without departing from the scope and spirit of the invention. Although the invention has been described in connection with specific preferred embodiments, it should not be unduly limited to such embodiments.

The purification strategy is based on the unique biochemical properties of vitamin K dependent proteins. E.g. in the Gla-domain about 12 negative charges are focused within a short amino acid stretch. This negative charge can be neutralized or even converted to positive charge by adding divalent cations (e.g. $Ca^{2+}$) to the system. Based on this effect, e.g. rFIX can be bound to ion-exchange resins at one specific charge state and eluted from the gel by converting the charge by removing (or adding) $Ca^{2+}$. This principle of separation is called "pseudo affinity chromatography". This principle is reflected also in those vitamin K dependent proteins which do not comprise a Gla-domain. The present inventive method which is applied for the purification of divalent cation binding proteins, like e.g. rFIX introduces pH shifts in the loadings, wash and/or eluate buffers to significantly improve the removal of product and process related impurities like inactive FIX species and CHO host cell proteins.

Purification Procedure of rFIX

The inventors developed a recombinant CHO cell line that expresses recombinant human Factor IX based on the CHO DXB11 parenteral cell line. The cell line was engineered in a way that it co-expresses recombinant human Furin to improve the intracellular maturation of pro-FIX to FIX. For the production process the cells are grown in suspension in chemostat mode and they were adapted to a chemically defined media without any addition of mammalian or plasma derived proteins. Soy peptone was added to the growth media to improve the productivity of the clone.

In a chemostat production campaign the collected cell culture harvest is clarified by depth filtration on Cuno depth filters (with positive zeta potential) and 0.2 pm membrane filtration on PVDF or PES filter membranes to removes cells and cell debris. The filtered cell free harvest represents the starting material for developing the purification process of rFIX.

EXAMPLE

The large scale purification process applied for the clinical production of rFIX starts with a capture step by Anion Exchange chromatography on Q-Sepharose Fast Flow loading the clarified harvest with a supplementation of 2 mM EDTA (see Table 1) and a pH of about 7.0-7.4. After loading (the load was cell free cell culture supernatant of an rFIX expressing CHO cell line) and wash 1, a low pH wash 2 is performed at pH 6.0 to remove inactive FIX species and bound CHO proteins. A third wash with low conductivity and a pH of 7.3-7.5 is performed to prepare the column for elution. Bound FIX is eluted from the column with a buffer containing Calcium and having a pH of 8.0 which is significantly above the pH of wash 2. This procedure results in a selective elution of FIX and a very low co-elution of product and process related impurities (inactive FIX species and CHO host cell protein). About 99.5% of the CHO HCP proteins applied to the column were removed (CHO HCP reduction factor approximately 190) at this step and the specific activity of FIX increased by a factor of about 1.5. Table 2 below summarizes the composition of the buffers for the Q-Sepharose Capture step (first anion exchange step).

On the eluate pool of the first Anion exchange purification step a solvent/detergent virus inactivation is performed by adding 1% Triton X-100, 0.3% tri-n-butyl phosphate and 0.3% Polysorbate 80. The S/D treated FIX solution is then diluted with a calcium containing buffer to adjust the calcium concentration to about 6 mM and reduce the conductivity to 15-18 mS/cm (RT). The pH of the solution slightly drops from 8.0 to about 7.6-7.8.

The S/D treated and diluted FIX solution is then applied to the first polishing step on Q-Sepharose Fast Flow which does not bind FIX under the conditions applied (see Table 3 below). Residual CHO host cell protein (CHO HSP) can bind to the Anion Exchange resin due to the higher pH compared to wash 2 (Capture step on Q-Sepharose Fast Flow) and the lower conductivity compared to the eluate pool of the capture step.

The results which were obtained with this improved purification method are summarized in Tables 4 and 5 below; tables 4 and 5 represent the results of two subsequently performed runs.

TABLE 1

Final purification scheme for FIX Capture on Q Sepharose Fast Flow (first anion exchange step)

| Step | Buffer | Amount CV | Flow rate cm/h | Comment |
|---|---|---|---|---|
| 1 resin activation | QFF-activation | 2.0 | 150 | |
| 2 equilibration | QFF-Equi | 4.0 | 150 | |
| 3 sample load | cell free CCS supplemented with 2 mM EDTA; | appr. 125 CV | 150 | Loading: 0.5-1.2 mg FIX Ag/ml resin |
| 4 wash 1 | QFF-Equi | 2.0 | 150 | |
| 5 wash 2 | QFF-Wash | 5.0 | 100 | |
| 6 wash 3 | QFF-Equi | 2.0 | 100 | |
| 7 elution | QFF elu | 5.0 | 50 | Collecting starts after 0.5 CV and ends after 5 CV |

The flow rates suggested are based on column bed height of 20 cm; all steps are performed at 2-8° C.
CCS: Cell culture supernatant

TABLE 2

Composition of buffers for the Q-Sepharose Capture step

| | Buffer/Step | Composition | Conductivity [mS/cm] at RT |
|---|---|---|---|
| | Resin activation, QFF-act | 2000 mM NaCl | n.d. |
| equilibration | equilibration, wash, QFF-Equi | 20 mM Tris, 2 mM EDTA, pH = 7.4 ± 0.2 at RT | 1.5-2.5 |
| wash | wash QFF-wash | 20 mM MES, 180 mM NaCl, 2 mM EDTA, pH = 6.0 ± 0.2 at RT | 16.5-19 |
| elution | QFF-Elu | 20 mM Tris, 180 mM NaCl, 2 mM CaCl$_2$, pH = 8.0 ± 0.2 at RT | 17-22 |
| EDTA stock | EDTA | 200 mM EDTA | | n.d. = not determined

TABLE 3

Purification scheme for FIX polishing step on Q Sepharose Fast Flow (second anion exchange step)

| Step | Buffer | Amount CV | Flow rate cm/h | Comment |
|---|---|---|---|---|
| 1 | resin activation | 2 M NaCl | >5.0 | 76 |
| 2 | equilibration | QFF equi-buffer | >4.0 | 76 |
| 3 | sample load | S/D treated and diluted rFIX pool* | appr. 300 liter | 76 | loading: 0.5-1.5 mg FIX Ag/ml resin |
| 4 | wash 1 | QFF equi-buffer | 0, 75 | 76 |

The flow rates suggested are based on column bed height of 20 cm; all steps are performed at 2-15° C. During loading the product will not bind to the resin and be collected in the column flow-through by combining the fractions column effluent and wash 1.
*conductivity approximately 18 mS/cm (RT)

TABLE 4

Results after two anion exchange steps - run A

| | FIX clotting step yield % | FIX Antigen step yield % | FIX specific activity Units Clotting/mg FIX Ag | CHO HCP reduction* ratio | CHO HCP impurity μg/mg FIX Ag | CHO DNA pg/ml |
|---|---|---|---|---|---|---|
| Load QFF_01 | — | — | 160 | — | 1200 | 28000 |
| Eluate QFF_01 | 104 | 93 | 270 | 229 | 7.7 | <1 |
| Effluent QFF_02 | 98 | 101 | 275 | 1.75 | 4.6 | <1 |

TABLE 5

Results after two anion exchange steps- run B

| | FIX clotting step yield % | FIX Antigen step yield % | FIX specific activity Units Clotting/mg FIX Ag | CHO HCP reduction* ratio | CHO HCP impurity μg/mg FIX Ag | CHO DNA pg/ml |
|---|---|---|---|---|---|---|
| Load QFF_01 | — | — | 157 | — | 1200 | 3000 |
| Eluate QFF_01 | 103 | 90 | 296 | 215 | 9.2 | <1 |
| Effluent QFF_02 | 101 | 96 | 290 | 1.7 | 6.4 | <1 |

*CHO HCP reduction ratio: calculated as a quotient of CHO HCP loaded onto the column over CHO HCP protein found in the eluate calculated from total mg

The invention claimed is:

1. A method for the purification of a divalent cation binding protein comprising the steps of:
   (a) loading a first anion exchange resin material with the divalent cation binding protein in a loading buffer in the absence or low concentration of divalent cations, wherein the loading buffer has a pH of 6.8 to 7.5;
   (b) performing at least three wash steps with at least three washing buffers in the absence of a divalent cation but in the presence of a counter-anion, wherein the washing buffer of the second wash step has a pH of 5.5 to 6.5 and a conductivity of between 16 and 18 mS/cm, the washing buffer of the third wash step does not contain any salt, and the loading buffer and the washing buffer of the first wash step have the same pH and conductivity;
   (c) eluting the divalent cation binding protein with an eluant comprising a divalent cation and a counter-anion to form an eluate pool containing the divalent cation binding protein, wherein the eluant has a pH of 7.5 to 8.5, wherein the eluant has a pH at least 0.5 pH units higher than the pH of the loading buffer, and wherein the eluant has a conductivity between 16 and 25 mS/cm;
   (d) forming an eluate by diluting the obtained eluate pool, and increasing the concentration of the divalent cation relative to the eluate pool;
   (e) loading a second anion exchange resin material with the eluate obtained in step (d); and
   (f) collecting flow-through from the second anion exchange resin material containing the divalent cation binding protein, wherein the divalent cation binding protein in the flow-through is at least 99% w/w pure with respect to host cell protein impurities.

2. The method according to claim 1, wherein the washing buffer of the first wash step and the washing buffer of the third wash step have a pH that is at least 0.5 pH units lower than the pH of the eluant of step (c).

3. The method according to claim 1, wherein the eluant in step (c) has a conductivity higher than the conductivity of the loading buffer in step (a) and wherein the eluate in step (d) has a conductivity that is lower than the conductivity of the eluant in step (c).

4. The method according to claim 1, wherein the at least one divalent cation in step (b) is selected from the group consisting of $Ca^{2+}$, $Be^{2+}$, $Ba^{2+}$, $Mg^{2+}$, $Mn^{2+}$, $Sr^{2+}$, $Zn^{2+}$, $Co^{2+}$, $Ni^{2+}$, and $Cu^{2+}$, and a combination thereof.

5. The method according to claim 1, wherein the divalent cation binding protein is a calcium binding protein.

6. The method according to claim 1, wherein the divalent cation binding protein is a vitamin K-dependent protein.

7. The method according to claim 1, wherein the divalent cation binding protein is selected from the group consisting of Factor II, Factor VII, Factor IX, Factor X, Protein C, Protein S, Annexin and calmodulin.

8. The method according to claim 1, wherein the washing buffer of the third wash step has a pH of 7.0 to 8.2.

9. The method according to claim 1, wherein the washing buffer of the first wash step has a pH of 7.3 to 7.5, the washing buffer of the second wash step has a pH of 5.5 to 6.5 or pH of 5.9 to 6.1, and the washing buffer of the third wash step has a pH of 7.3 to 7.5.

10. The method according to claim 1, wherein the pH of the eluate in loading step (e) is higher than either the pH of the loading buffer in loading step (a) or the pH of the washing buffer of the second wash step.

11. The method according to claim 1, wherein the conductivity of the eluate in loading step (e) is equal to or lower than the conductivity of the washing buffer of the second wash step.

12. The method according to claim 7, wherein the divalent cation binding protein is (r)FIX.

13. The method of claim 12, wherein the (r)FIX has a specific activity of at least 270 IU/mg FIX Ag.

14. The method according to claim 1, wherein the loading buffer in loading step (a) has a pH of 7.0 to 7.5, and wherein the washing buffer of the second wash step has a pH of 5.5 to 6.5.

15. The method according to claim 1, wherein at least one of the group consisting of the loading buffer of step (a) and the washing buffer of any of the at least three wash steps has a pH that is at least 0.5 pH units lower than the pH of the eluant of step (c).

16. The method of claim 13, wherein the (r)FIX has a specific activity selected from the group consisting of 270 to 350 IU/mg FIX Ag, 270 to 320 IU/mg FIX Ag, and 280 to 300 IU/mg FIX Ag.

17. The method of claim 1, wherein the divalent cation binding protein is at least 99.5% w/w pure with respect to host cell protein impurities.

* * * * *